United States Patent [19]
Lafferty et al.

[11] Patent Number: 5,411,500
[45] Date of Patent: May 2, 1995

[54] PORTABLE ARTHROSCOPE WITH DISPOSABLE PROBE

[75] Inventors: Michael Lafferty, Leucadia; Daniel Kline, Carlsbad; Charles S. Slemon, Encinitas, all of Calif.

[73] Assignee: Sofamor Danek Properties, Inc., Memphis, Tenn.

[21] Appl. No.: 949,763

[22] Filed: Sep. 23, 1992

Related U.S. Application Data

[63] Continuation of Ser. No. 651,746, Feb. 4, 1991, abandoned.

[51] Int. Cl.$^6$ .............................................. A61B 17/36
[52] U.S. Cl. ..................................... 606/2; 128/6; 606/14; 606/15
[58] Field of Search ............................. 606/2, 10–17; 128/2, 4

[56] References Cited

U.S. PATENT DOCUMENTS

| | | | |
|---|---|---|---|
| 4,253,448 | 3/1981 | Terada | 128/6 X |
| 4,589,404 | 5/1986 | Barath et al. | 128/6 |
| 4,590,923 | 5/1986 | Watanabe | 128/6 |
| 4,607,622 | 8/1986 | Fritch et al. | 128/6 |
| 4,620,769 | 11/1986 | Tsuno | 128/6 |
| 4,736,733 | 4/1988 | Adair | 128/6 |
| 4,754,328 | 6/1988 | Barath et al. | 358/98 |
| 4,755,873 | 7/1988 | Kobayashi | 128/6 X |
| 4,844,071 | 7/1989 | Chen et al. | 128/6 |
| 4,865,029 | 9/1989 | Pankratov | 606/7 |
| 4,920,961 | 5/1990 | Grossi et al. | 606/14 |
| 4,947,245 | 8/1990 | Ogawa et al. | 128/6 X |

*Primary Examiner*—Peter A. Aschenbrenner
*Attorney, Agent, or Firm*—Woodard, Emhardt, Naughton, Moriarty & McNett

[57] ABSTRACT

A hand-held portable arthroscope has a housing and a disposable cap removably attached to the distal end of the housing. A probe which includes a fiber optic image guide and a plurality of optical illuminating fibers is mounted on the cap, and is insertable into a body for imaging the internal structure of the body. The illuminating fibers extend through the cap and are connected in light communication with a quartz halogen lamp for illuminating the internal body structure being imaged. To gather light from the illuminated internal structure of a body into which the probe has been inserted, a GRIN rod is attached to the distal end of the image guide. Focussing optics are mounted in the housing in light communication with the image guide. These focussing optics are axially movable within the housing for focussing the image from the image guide. Light which passes through the focussing optics enters a camera head which is also mounted in the housing. The camera head is in turn electrically connected to a video display device for producing an image of the internal structure of the body.

13 Claims, 1 Drawing Sheet

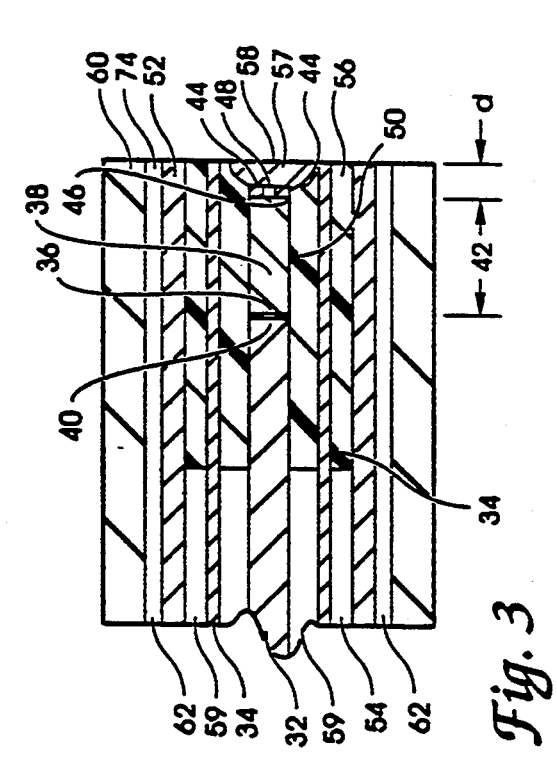
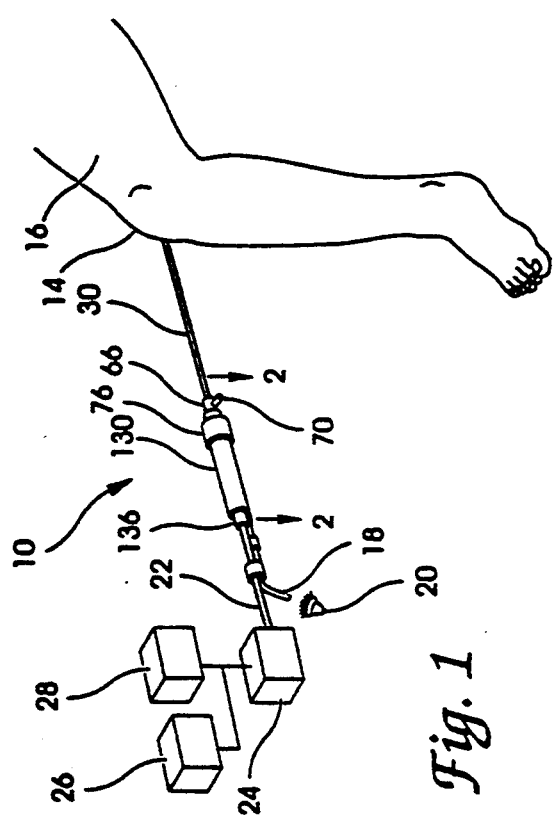
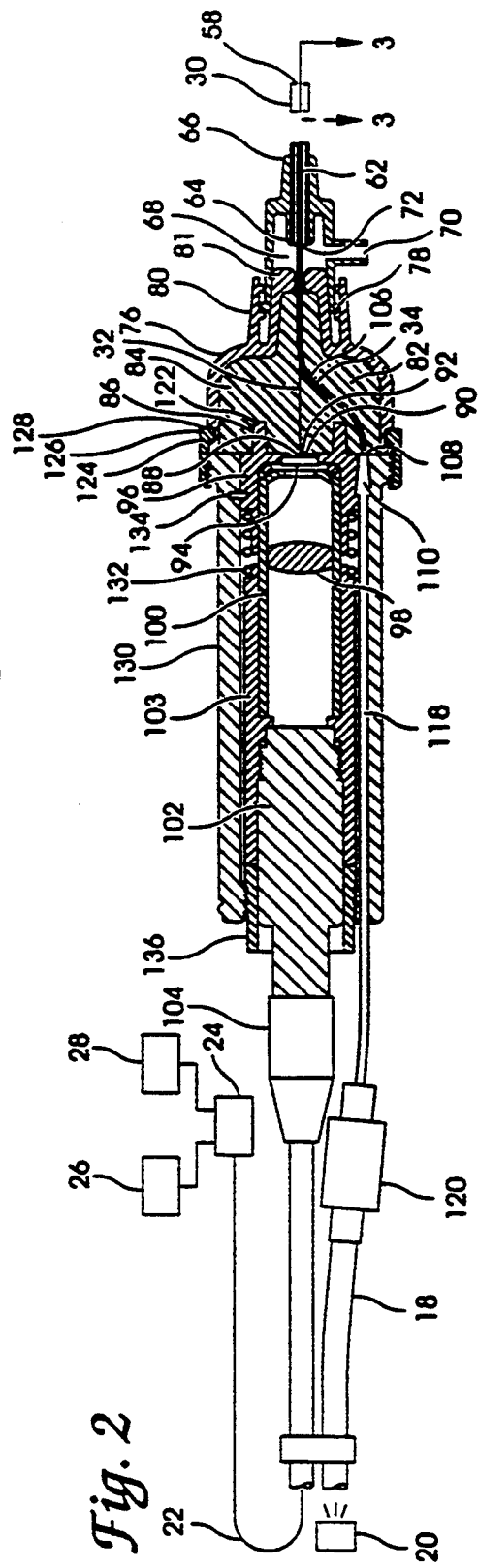

PORTABLE ARTHROSCOPE WITH DISPOSABLE PROBE

This is a continuation of application Ser. No. 07/651,746, filed on Feb. 4, 1991, now abandoned.

FIELD OF THE INVENTION

The present invention relates generally to medical diagnostic devices. More particularly, the present invention relates to arthroscopes. The present invention particularly, though not exclusively, relates to hand-held portable arthroscopes with disposable probe assemblies.

BACKGROUND OF THE INVENTION

Modern surgical techniques which are relatively non-invasive have been recently developed for diagnosing and correcting damage to the interior structure of body parts, e.g., bone joints. Among the most common of these modern surgical techniques is arthroscopy, which can be used for examining the interior structure of a body joint, for example, a knee, in order to diagnose maladies of the joint. In other words, arthroscopy permits viewing the internal structure of a body joint without requiring conventional and relatively invasive surgery on the joint. If required, relatively non-invasive corrective surgery can be performed in conjunction with arthroscopic examination techniques to repair joint damage which is discovered during the examination.

Arthroscopic examination typically involves inserting a probe into the joint to be examined. The probe assembly has an imaging device attached to it, and the imaging device is in turn connected to a video display for generating a picture of the interior structure of the joint. Consequently, the operator of the arthroscope is able to view, in real-time, the interior structure of the joint as the probe is inserted into the joint. By viewing the internal structure of the joint, a diagnosis of the joint's potential maladies can be made and appropriate treatment prescribed.

It is the case that existing arthroscopes require support equipment that is relatively large and bulky and is typically used in an operating room environment. Consequently, these arthroscopes cannot be easily moved from one location to another, as may occasionally be required in a medical establishment. Furthermore, arthroscopes which require sizable support equipment are ordinarily expensive devices, and their relatively high cost can make arthroscopic examination economically prohibitive for some patients. The present invention recognizes that an arthroscope need not necessarily require large and expensive support equipment and that there is a need to provide an arthroscope which can be used in a Doctor's office for diagnosis of a joint injury. Further, there is a recognized need to provide an arthroscope with a sufficiently small disposable probe so that only a local anesthetic is necessary.

Additionally, the probes of existing arthroscopes are typically reusable devices and must accordingly be sterilized before each use, in order to eliminate the possibility of infecting the patient with a contaminated probe. Unfortunately, the possibility remains that a reusable probe may not be effectively sterilized and can accordingly remain septic, or that a properly sterilized probe could become septic in the time period between sterilization and use of the probe. The present invention recognizes that an arthroscope can be provided which uses a non-reusable disposable probe to substantially reduce the likelihood of transmitting infections.

Accordingly, it is an object of the present invention to provide an arthroscope which is portable and hand-held. It is a further object of the present invention to provide an arthroscope which has a disposable probe that is insertable into a body joint for generating a real-time picture of the joint. Finally, it is an object of the present invention to provide an arthroscope which is relatively inexpensive to manufacture and comparatively easy and cost-effective to use.

SUMMARY

A portable diagnostic arthroscope has a hand-held generally cylindrical hollow housing and a disposable cap which is removably attached to the distal end of the housing. The disposable cap includes an elongated probe which is insertable into a body joint. The probe is mounted on the cap and extends outwardly from the cap away from the housing. The disposable probe also includes a hollow tubular steel cannula which surrounds a cylindrically-shaped GRIN rod that is mounted on a scope needle. This scope needle is incorporated with the disposable probe and is positioned inside the cannula with the GRIN rod near the cannula's open distal end. Light which is reflected by the interior structure of the joint enters the distal base of the cylindrically-shaped GRIN rod and is focussed by the GRIN rod onto the GRIN rod's proximal base. To transfer the light back through the disposable probe, the proximal base of the GRIN rod is attached to a fiber optic image guide which is also positioned inside the scope needle, so that light which enters the distal base of the GRIN rod is essentially focussed by the GRIN rod onto the image guide. Also, to illuminate the interior of the joint, a plurality of optical illumination fibers are mounted within the scope needle and are positioned next to the image guide.

The image guide extends through the scope needle of the probe and through the cap and is optically joined to focussing optics which are mounted in the housing. The focussing optics are axially movable within the nondisposable housing for focussing a camera head which is also mounted in the housing. The camera head is, in turn, electrically connected to a camera control unit which is external to the arthroscope. In accordance with the present invention, the camera control unit can control a CRT or other visual display device to display the image of the internal structure of the joint.

The illumination fibers in the disposable cap also extend through the scope needle and cap and are optically joined with a first end of an optical cable that is mounted inside the nondisposable housing. The second end of the optical cable can be irradiated with light from a quartz halogen lamp or some other light source which may be located either in the disposable scope assembly, in the housing or externally to the housing. Thus, light from the light source can be transmitted through the optical cable and illumination fibers to illuminate the internal structure of the joint. As envisioned by the present invention the probe and cannula, together with the probe needle, image guide and illuminating fibers are optically joined to the housing and its components and are collectively disengageable therefrom for disposal after use.

The novel features of this invention, as well as the invention itself, both as to its structure and its operation,

BRIEF DESCRIPTION OF THE DRAWINGS

FIG. 1 is a perspective view of the novel portable arthroscope of the present invention, seen in its intended environment;

FIG. 2 is a partial cross-sectional view of the novel portable arthroscope of the present invention, as seen along the line 2—2 in FIG. 1 with the distal portion of the probe shown in full side view; and FIG. 3 is an enlarged cross-sectional view of the distal end of the probe of the novel portable arthroscope as seen along the line 3—3 in FIG. 2.

DESCRIPTION OF THE PREFERRED EMBODIMENT

Referring initially to FIG. 1, a portable hand-held arthroscope is shown, generally designated 10. As shown, arthroscope 10 is being used to examine the internal structure of the knee 14 of a patient 16. Arthroscope 10 is attached in light communication via optical line 18 to a quartz halogen lamp 20. While the present invention envisions use of a lamp 20 which is a quartz halogen lamp for economy, it is to be understood that lamp 20 may alternatively be any other suitable light source well known in the art, e.g., a xenon gas bulb. Further, it is to be appreciated that lamp 20 need not necessarily be externally located relative to arthroscope 10 but may instead be included as a component of the arthroscope 10. FIG. 1 also shows that arthroscope 10 is electrically connected via line 22 to a camera control unit 24. Camera control unit 24 can be electrically connected to a cathode ray tube (CRT) 26 and a video camera recorder (VCR) 28, as shown in FIG. 1, for respectively displaying and recording a video image of the internal structure of knee 14.

Now referring to FIGS. 2 and 3, the details of arthroscope 10 can be seen. As shown in FIG. 2, arthroscope 10 includes a probe 30 which is insertable into knee 14 (shown in FIG. 1). FIG. 3 shows that probe 30 includes a scope needle 52 which holds an optical fiber image guide 32 and a plurality of optical illuminating fibers 34 which are positioned radially in scope needle 52 around image guide 32. Preferably, both image guide 32 and illuminating fibers 34 are optical fibers which have relatively large numerical apertures (NA). Additionally, image guide 32 is preferably short, i.e., the length of image guide 32 is preferably less than about eight (8) inches.

As shown in FIG. 3, the proximal end 36 of a (GRIN) rod 38 is bonded to the distal end 40 of image guide 32. Preferably, GRIN rod 38 is a type of internally-refractive lens made of thallium-doped glass manufactured by Nippon Sheet Glass. In accordance with the present invention, the length 42 of GRIN rod 38 establishes the focussing characteristics of GRIN rod 38 as appropriate for the particular application of arthroscope 10.

FIG. 3 also shows that an iris 44 of opaque material is deposited on distal end 46 of GRIN rod 38 to reduce optical aberrations. As shown, iris 44 has an opening 48 to permit the passage of light into GRIN rod 38. If desired, the side surface 50 of GRIN rod 38 can also be covered with an opaque layer to reduce stray light which could otherwise enter GRIN rod 38 through side surface 50.

Still referring to FIG. 3, probe 30 is shown to include a hollow scope needle 52 which has a lumen 54. As shown, needle 52 is positioned in a surrounding relationship with image guide 32 and illuminating fibers 34. Needle 52 is preferably a hollow 16-gauge stainless steel tube, and image guide 32 and illuminating fibers 34 are positioned in the lumen 54 of needle 52. The portion of lumen 54 which surrounds image guide 32 and illuminating fibers 34 is filled with an opaque epoxy material 56, to cushion and support image guide 32 and illuminating fibers 34. FIG. 3 also shows an area at the distal end 46 of GRIN rod 38 which is covered by a clear epoxy material 57. The end 58 of opaque epoxy material 56 and clear epoxy material 57 is preferably polished. As shown, in order to provide protection for GRIN rod 38, the distal end 46 of GRIN rod 38 is recessed a distance d from end 58. FIG. 3 also shows that lumen 54 creates a hollow space 59 proximal to the end 58 of scope needle 52 to prevent collateral damage to probe 30 should probe 30 be inadvertently bent. In the preferred embodiment, distance d is approximately five thousandths of an inch.

FIG. 3 further shows that probe 30 includes a 14-gauge hollow stainless steel cannula 60 which is positioned in a surrounding relationship to needle 52. Cannula 60 defines a passageway 62 between cannula 60 and needle 52.

Referring back to FIG. 2, the cannula 60 of probe 30 is shown attached to a disposable injection-molded hub 66 near proximal end 64 of cannula 60. Hub 66 is formed with a chamber 68, and fluid can be infused into chamber 68 through fluid port 70 from a fluid source (not shown). Fluid in chamber 68 can enter open end 72 of cannula 60 and pass through passageway 62. This fluid can subsequently be flushed out of open end 74 (shown in FIG. 3) of cannula 60 to bathe the internal structure of knee 14 to provide a clear viewing field for probe 30 when probe 30 is inserted into knee 14.

Hub 66 is engaged with a disposable hollow injection-molded cap 76, as shown in FIG. 2. More specifically, bulb portion 81 of cap 76 extends into hub 66, and luer ears 78 of hub 66 can be threadably engaged with luer fitting 80 of cap 76. As shown in FIG. 2, cap 76 has a chamber 82, and chamber 82 is filled with a resilient epoxy material 84. Epoxy material 84 is in turn formed with key guides 86. As shown in FIG. 2, image guide 32 extends through epoxy material 84, and the end 88 of image guide 32 is substantially coplanar with surface 90 of epoxy material 84. In accordance with the present invention, surface 90 is polished to a smooth finish to establish an image plane 92.

Light from image guide 32 which passes through image plane 92 impinges upon a transparent sapphire window 94. FIG. 2 shows that light which has passed through window 94 enters focussing optics 98, which are mounted inside an optics base 100. Focussing optics 98 magnify the light approximately seven times (7×) and focus the light onto a camera head 102. Camera head 102, in the preferred embodiment, is a charged coupled device (CCD).

In accordance with the present invention, camera head 102 converts the light image from optics 98 to an electrical signal representative of the internal structure of knee 14. This electrical signal is coupled into an appropriate electrical connector 104. As disclosed above, the electrical signal is conducted by line 22 to CCU 24 for further processing.

FIG. 2 also shows that illuminating fibers 34 extend through epoxy material 84 in a fiber bundle 106 to end 88 of epoxy material 84. As shown, end 108 of fiber bundle 106 is juxtaposed with a taper 110. It is to be understood in reference to FIG. 2 that taper 110 diminished from a diameter which is approximately twice as large as the diameter of bundle 106, for optimizing the illumination pattern within knee 14 which is established by illuminating fibers 34. Alternatively, a GRIN rod can be used instead of taper 110. In either case the taper 110 or the substituted GRIN rod is connected to optical continuation fiber 118. For the embodiment shown, the large base of the taper 110 is attached to continuation fiber 118 and the small base of the taper 110 is optically connected to the illuminating fibers 34. Continuation fiber 118 is in turn coupled to an optical connector 120, and optical connector 120 is attached in light communication with lamp 20 through optical line 18. As suggested above, the light source 20 can be actually located in housing 130.

The cooperation of structure of arthroscope 10 is shown in FIG. 2 to include a keyed engagement between front tube 96 and epoxy material 84. More specifically, keys 122 of front tube 96 engage key guides 86 of epoxy material 84 to establish a predetermined orientation of front tube 96 relative to epoxy material 84. This predetermined orientation ensures that the optical components in cap 76 are properly aligned with associated optical components in front tube 96 when cap 76 is joined to front tube 96. Furthermore, an annular clamping ring 124 is shown which has an annular abutment 126 formed thereon for slidingly engaging groove 128 in cap 76. As shown in FIG. 2, clamping ring 124 can be threadably engaged with a housing 130 for holding cap 76 against housing 130. Housing 130, in turn, supports front tube 96 and front tube extension 103 in an interference fit. In accordance with the present invention, front tube 96 is fixedly mounted in housing 130, while front tube extension 103 is slidably mounted in housing 130. More specifically, a retaining screw 134 is threaded into both housing 130 and front tube 96 to fixedly hold front tube 96 within housing 130.

FIG. 2 also shows that a preload spring 132 is positioned between front tube 96 and front tube extension 103 to urge front tube extension 103 proximally away from front tube 96 to permit focussing the image from image guide 32, as disclosed more fully below. Also, FIG. 2 shows that a focussing ring 136 is threadably engaged with housing 130 and is positioned against front tube extension 103. Accordingly, focussing ring 136 can be rotated as appropriate to axially move front tube extension 103 relative to housing 130 and image plane 92. For example, when focussing ring 136 is rotated clockwise, ring 136 urges front tube extension 103 distally relative to image plane 92 (i.e., toward the right in FIG. 2). On the other hand, when focussing ring 136 is rotated counterclockwise, preload spring 132 urges front tube extension 103 against ring 136 to move front tube extension 103 proximally away from front tube 96 relative to image plane 92 (i.e., toward the left in FIG. 2). Recall that camera head 102 and optics base 100 are fixedly mounted on front tube extension 103. Consequently, as front tube extension 103 is moved axially relative to housing 130, camera head 102 and optics base 100 also move axially relative to housing 130 (and, hence, image plane 92) to focus the image present on image plane 92.

OPERATION

In the operation of arthroscope 10, reference is made to FIGS. 1 and 2. Housing 130 of arthroscope 10 is initially connected to lamp 20 via optical line 18. Also, housing 130 of arthroscope 10 is connected to camera control unit 24 via electrical line 22. Disposable cap 76 is first attached to housing 130, but hub 66 with cannula 60 are initially disconnected from cap 76. A trocar (not shown) is positioned through hub 66 and cannula 60 and inserted into knee 14 to establish an entry site for cannula 60 into knee 14. Cannula 60 is then inserted into knee 14, the trocar is removed from cannula 60, and hub 66 with cannula 60 is joined to disposable cap 76.

Once probe 30 is positioned in the knee 14 and cap 76 engaged with housing 130, the image of the internal structure of knee 14 is transmitted through GRIN rod 38 and image guide 32 to image plane 92. The image present at image plane 92 is processed as disclosed above by focussing optics 98 and camera head 102 and sent to camera control unit 24 via line 22. Camera control unit 24 causes the image to be displayed on CRT 26 or recorded by VCR 28, as appropriate.

If desired, the image from image plane 92 can be focussed by appropriately rotating focussing ring 136 to move front tube extension 103 (and, hence, optics 98) axially relative to front tube 96 (and, hence, axially relative to image plane 92). After examination of knee 14, probe 30 is withdrawn from knee 14 and cap 76 detached from housing 130 and disposed of in a suitable receptacle. A new cap 76 (not shown) can be engaged with housing 130 for subsequent examination of a patient using arthroscope 10.

In order to maintain a sterile environment for the arthroscope 10, a flexible sleeve (not shown) can be attached to the distal end of housing 130 and draped over the housing 130. Importantly, this sleeve must allow the operator tactile contact with the operative components of arthroscope 10. The sleeve, like the probe 30 and its contents is disposable.

While the particular arthroscope with disposable probe as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A hand-held diagnostic arthroscope with disposable probe for examining an internal structure of a body, which comprises:

a hollow housing;

an image guide having a distal end and a proximal end;

a lens attached to said distal end of said image guide for gathering light from the internal structure of the body;

an optical illumination fiber joined with said image guide to establish a disposable probe having a distal end and a proximal end, said proximal end of said probe being detachably connected to said housing;

a rigid tubular needle surrounding and supporting said image guide and said illumination fiber;

a light source in light communication with said optical illumination fiber for illuminating said internal structure of said body;

a camera head positioned in said housing in light communication with said proximal end of said image guide for generating a visual display signal representative of said illuminated structure of said body;

a light focussing means positioned in said housing and a disposable cap detachably attached to said distal end of said housing for supporting said disposable probe and removably connecting said disposable probe to said housing, said image guide extending through said cap and juxtaposed with said focussing means when said cap is attached to said distal end of said housing;

a rigid tubular cannula having a lumen, said needle being positioned in said lumen coaxially with said cannula to establish an annular fluid passageway between said needle and said cannula; and alignment means for aligning said image guide with said focussing means and for aligning said optical illumination fiber in light communication with said light source when said disposable cap is attached to said housing.

2. A hand-held diagnostic arthroscope for examining an internal structure of a body as recited in claim 1, wherein said probe further comprises a hollow tubular cannula having a lumen, said needle being positioned in said lumen coaxially with said cannula to establish an annular fluid passageway between said needle and said cannula, and said arthroscope further comprises a source of liquid attached in fluid communication with said passageway for bathing said internal structure of said body with said liquid.

3. A hand-held portable arthroscope with disposable probe, which comprises:

an elongated disposable probe having a proximal end and a distal end insertable into a body for examining the internal structure thereof, said probe comprising a plurality of optical illumination fibers in light communication with a light source probe for illuminating said internal structure, said probe further comprising an optical fiber image guide having a distal end and a gradient refractive index rod attached to said distal end and a plurality of optical fibers in light communication with said image guide for gathering light from said illuminated structure and guiding said light through said probe, wherein said probe further comprises a tubular needle surrounding said image guide for supporting said image guide and a hollow tubular cannula having a lumen, said needle being positioned in said lumen coaxially with said cannula to establish an annular fluid passageway between said needle and said cannula;

a hand-held housing having a distal end detachably connected to said proximal end of said disposable probe for supporting said disposable probe, said housing including a camera in light communication with said image guide for generating a signal representative of said light from said internal structure;

a light focussing means positioned in said housing and a disposable cap removable attached to said distal end of said housing for supporting said disposable probe and connecting said disposable probe to said housing, said image guide extending through said cap and juxtaposed with said focussing means when said cap is attached to said distal end of said housing;

alignment means for aligning said image guide in juxtaposition with said focussing means and said optical illumination fibers in light communication with said light source; and a source of liquid attached in fluid communication with said passageway for bathing said internal structure of said body with said liquid.

4. A hand-held portable arthroscope as recited in claim 3, wherein said housing has a distal end and said arthroscope further comprises a light focussing means positioned in said housing and a disposable cap removably attached to said distal end of said housing for supporting said probe and connecting said probe to said housing, said image guide extending through said cap and juxtaposed with said focussing means when said cap is attached to said distal end of said housing.

5. A hand-held portable arthroscope as recited in claim 3, further comprising a video device electrically connected to said camera head for generating a video display representative of said signal from said camera head.

6. A hand-held portable arthroscope as recited in claim 3, wherein said light source is a quartz halogen lamp, and said light focussing means is axially movable within said housing for focussing light from said image guide.

7. A hand-held diagnostic arthroscope for examining an internal structure of a body as recited in claim 2 wherein said illumination fiber extends through said cap and has a proximal end abutting said housing.

8. A hand-held diagnostic arthroscope for examining an internal structure of a body as recited in claim 7 wherein a resilient resin material is positioned between said image guide and said cap in adherence therewith thereby fixably encasing said image guide and said illumination fiber within said cap.

9. An optical scope having a light source and a camera for viewing an internal structure of a body, including a disposable probe which comprises:

an image guide having a distal end and a proximal end;

an optical illumination fiber having a distal end and a proximal end, said illumination fiber being juxtaposed with said image guide;

a lens attached to said distal end of said image guide for gathering light from the internal structure of the body;

a hollow tubular needle surrounding said image guide and said illumination fiber for supporting said image guide and said illumination fiber;

alignment means for aligning said proximal end of said optical illumination fiber in light communication with said light source to illuminate said internal structure of said body, and for aligning said proximal end of said image guide in light communication with said camera to generate a visual display signal representative of said illuminated structure of said body, said alignment means being attached to said tubular needle for engagement with said camera and said light source;

a hollow tubular cannula having a lumen, said needle being positioned in said lumen coaxially with said cannula to establish an annular fluid passageway between said needle and said cannula; and a source of liquid attached in fluid communication with said passageway for bathing said internal structure of said body with said liquid.

10. A disposable optical probe attachable to an optical viewing means, said probe comprising:
   an image guide having a proximal end and a distal end;
   an optical illumination fiber having a distal end and a proximal end, said illumination fiber being juxtaposed with said image guide;
   a rigid tubular needle surrounding said image guide and said illumination fiber wherein said needle has an outer surface, said needle supporting said image guide and said illumination fiber;
   a lens attached to said distal end of said image guide for gathering light from the internal structure of the body, said lens having a distal end;
   an iris of opaque material deposited on the distal end of said lens, said iris partially covering said distal end of said lens to reduce optical aberrations;
   a layer of clear epoxy material covering said distal end of said lens and said iris on said distal end;
   a rigid tubular cannula surrounding said needle, said cannula having an inner surface, said inner surface of said cannula and said outer surface of said needle defining an annular fluid passageway;
   a connector attached to said cannula, said connector allowing selective attachment of said probe to said viewing means.

11. The disposable probe as recited in claim 10, said probe further comprising alignment means for aligning said probe relative to said viewing means.

12. The disposable probe as recited in claim 10 wherein said lens is a gradient refractive index rod and said image guide is an optical fiber.

13. The disposable probe as recited in claim 10 wherein said layer of epoxy material has a distal surface, said distal surface being polished.

* * * * *